United States Patent [19]
Kreder

[11] Patent Number: 5,776,081
[45] Date of Patent: Jul. 7, 1998

[54] URETHRAL PRESSURE CATHETER

[75] Inventor: Karl J. Kreder, Iowa City, Iowa

[73] Assignee: University of Iowa Research Foundation, Iowa City, Iowa

[21] Appl. No.: 467,100

[22] Filed: Jun. 6, 1995

[51] Int. Cl.$^6$ ................................................ A61B 5/103
[52] U.S. Cl. ................................................ 600/593; 600/587
[58] Field of Search ........................ 128/748, 762, 128/774, 673–675

[56] References Cited

U.S. PATENT DOCUMENTS

| | | | |
|---|---|---|---|
| Re. 30,966 | 6/1982 | Hargens et al. | 128/748 |
| 3,480,003 | 11/1969 | Crites | 128/2 |
| 4,063,548 | 12/1977 | Klatt et al. | 128/2 |
| 4,136,681 | 1/1979 | Hon | 128/2 |
| 4,191,196 | 3/1980 | Bradley et al. | 128/733 |
| 4,216,783 | 8/1980 | Kaiser et al. | 128/778 |
| 4,246,909 | 1/1981 | Wu et al. | 128/762 |
| 4,423,740 | 1/1984 | Castle et al. | 128/748 |
| 5,431,639 | 7/1995 | Shaw | 604/264 |

FOREIGN PATENT DOCUMENTS

| | | |
|---|---|---|
| 1 585 065 | 9/1970 | France . |
| 2 580 504 | 10/1986 | France . |
| 2 091 559 | 8/1982 | United Kingdom . |

*Primary Examiner*—Max Hindenberg
*Assistant Examiner*—Pamela Wingood
*Attorney, Agent, or Firm*—Elizabeth A. Hanley; Lawrence E. Monks; Lahive & Cockfield, LLP

[57] ABSTRACT

Devices and methods for measuring the weakness of body lumens, and in particular, urethral sphincters and similar valves, are disclosed. In one embodiment of the invention, a catheter with a hollow fluted distal end can be inserted into a lumen. The hollow fluted distal end of the catheter is then expanded into an enlarged configuration. The measurement of resistance to withdrawal of the catheter in the enlarged configuration provides an indication of weakness of the lumen. In one aspect of the invention, the catheter is inserted into a bladder via the urethral sphincter and the weakness of the urethral sphincter is measured. In another aspect of the invention, a device for measuring weakness of a body lumen, such as a urethral sphincter and similar valves, can consist of a catheter with a hollow fluted distal end having of an array of wings, and an expanding means for radially expanding the wings into an enlarged configuration. Subsequent withdrawal of the catheter in the enlarged configuration encounter resistances which can be measured as an indication of the weakness of the body lumen, such as a urethral sphincter and similar valves. In still another aspect of the invention, a system for measuring weakness of a body lumen can consist of a catheter, a means for expanding a hollow fluted distal end of the catheter from a first configuration into a second enlarged configuration and means for measuring resistance to withdrawal of the catheter in the enlarged configuration as an indicator of weakness of the body lumen, such as the urethral sphincter and similar valves.

51 Claims, 4 Drawing Sheets

5,776,081

1

URETHRAL PRESSURE CATHETER

BACKGROUND OF THE INVENTION

The field of the present invention is the diagnostic measurement of the weakness of body lumens and, in particular, diagnostic methods and devices for the measurement of the intrinsic weakness of urethral sphincters and similar valves.

It is estimated that at least 10% of the population in the United States and perhaps as many as 30% of the nursing home residents suffer from some degree of urinary incontinence. One of the causes of urinary incontinence is the intrinsic weakness of the urethral sphincter.

Various devices and methods have been used to measure urethral sphincter activity. Such devices are often complicated and typically involve the use of electrodes or the measurement of pressure exerted on fluids in a catheter. For example, U.S. Pat. No. 4,063,548 by Klatt et al. discusses inserting a balloon attached to a catheter into the bladder, filling the balloon with fluid to exert pressure on the bladder and subsequently measuring sphincter activity with electrodes. U.S. Pat. No. 4,191,196 by Bradley et al. discusses inserting a fluid-filled catheter equipped with electrodes and conductors into the urethra, and plotting electrical signals derived from the urethral activity and fluid pressure variations in the catheter as the catheter is withdrawn from the urethra.

Accordingly, there is a need for simple diagnostic methods and devices for measuring the weakness of a body lumen and, in particular, the weakness of a urethral sphincter and similar valves.

SUMMARY OF THE INVENTION

Methods and devices for measuring the weakness of body lumens are disclosed and, in particular, for measuring the intrinsic weakness of urethral sphincters and similar valves. The present invention is based on the recognition that measuring the resistance to withdrawal of an expandable distal end of a catheter from a body lumen provides a simple test for diagnosing lumen weakness.

In one embodiment of the invention, a catheter with a hollow fluted distal end can be inserted into a lumen. The hollow fluted distal end of the catheter can be expanded into an enlarged configuration. The measurement of resistance to withdrawal of the catheter in the enlarged configuration can provide an indication of weakness of the lumen. In one aspect of the invention, the catheter is inserted into a bladder via the urethral sphincter and the weakness of the urethral sphincter is measured by withdrawing the catheter in the enlarged configuration.

In one embodiment, diagnostic methods are disclosed in which a retracting cable is disposed inside the catheter and simultaneously inserted into the bladder or other body lumen with the catheter such that a plunger at the distal end of the cable extends beyond the hollow fluted distal end of the catheter. The retracting cable can then be activated by pulling the plunger at the distal end of the cable back into the hollow end of the catheter. As the plunger is pulled into the catheter, a plurality of wings disposed at the catheter's distal end will be forced into an expanded configuration. The activation of the cable can be restricted to a predetermined extent by a set-screw disposed at the catheter's proximal end. This set-screw can be set for different levels of cable activation corresponding to different levels of expansion of the wings of the hollow fluted distal end of the catheter (e.g., to at least about 4 french). The resistance to catheter withdrawal can be measured manually or with a resistance monitor. The withdrawal of the catheter can be set at a pre-determined rate by coupling the catheter to a catheter withdrawal device. The catheter can be removed and thrown away. Alternatively, prior to insertion, the catheter can be surrounded with a disposable plastic sheath. After withdrawal of the catheter, the plastic sheath can be removed from the catheter and thrown away, and the catheter sterilized prior to reuse.

In another aspect of the invention, a device for measuring weakness of a body lumen, such as a urethral sphincter and similar valves, can consist of a catheter with a hollow fluted distal end carrying an array of wings, and an expanding means for radially expanding the wings into an enlarged configuration. Withdrawal of the catheter in the enlarged configuration encounters resistance that can be measured as an indication of the weakness of the body lumen, such as a urethral sphincter and similar valves.

The expanding means can consist of a retracting cable disposed inside the catheter with a plunger distal end extending beyond the hollow fluted distal end of the catheter. The expanding means can also include means for activating the cable such that the plunger distal end of the retracting cable is drawn back into the hollow distal end of the catheter and expands the wings of the hollow end of the catheter into the second enlarged configuration. The expanding means can further include a set-screw for restricting the extent of cable activation and thus, the catheter wing expansion to a predetermined extent. The plunger distal end can be shaped for easy insertion into a body lumen, such as the bladder. The resistance to the withdrawal of the catheter can be objectively measured manually or with a resistance monitor. In addition, the rate of withdrawal of the of the catheter can be pre-set by coupling the catheter to a catheter withdrawal device. The catheter can be disposable. Alternatively, the catheter can consist of a sterilizable material and can further include a surrounding disposable plastic sheath.

In still another aspect of the invention, a system for measuring weakness of a body lumen can consist of a catheter, a means for expanding a hollow fluted distal end of the catheter from a first configuration into a second enlarged configuration and means for measuring resistance to withdrawal of the catheter in the enlarged configuration as an indicator of weakness of the body lumen, such as the urethral sphincter and similar valves. The system can include a retracting cable with a plunger distal end extending beyond the hollow fluted distal end of the catheter and an activating means for drawing the plunger distal end of the cable back into the distal end of the catheter such that a plurality of wings disposed at the hollow end of the catheter are expanded. A set-screw disposed at a proximal end of the catheter can restrict the activation of the retracting cable to a pre-determined extent. The plunger distal end can be shaped to facilitate easy insertion into a body lumen, such as bladder. The hollow fluted distal end of the catheter can include an array of radially disposed wings such that they are closed in a first configuration and radially expanded into a second enlarged configuration. The system can also include a catheter withdrawal means for withdrawing the catheter at a pre-determined rate. The catheter can be disposable. Alternatively, the catheter can consist of a sterilizable material and can further include a surrounding disposable plastic sheath.

BRIEF DESCRIPTION OF THE DRAWINGS

FIGS. 2A through 2B also illustrate a set-screw for limiting the extent of this activation.

DETAILED DESCRIPTION

Figure 1:
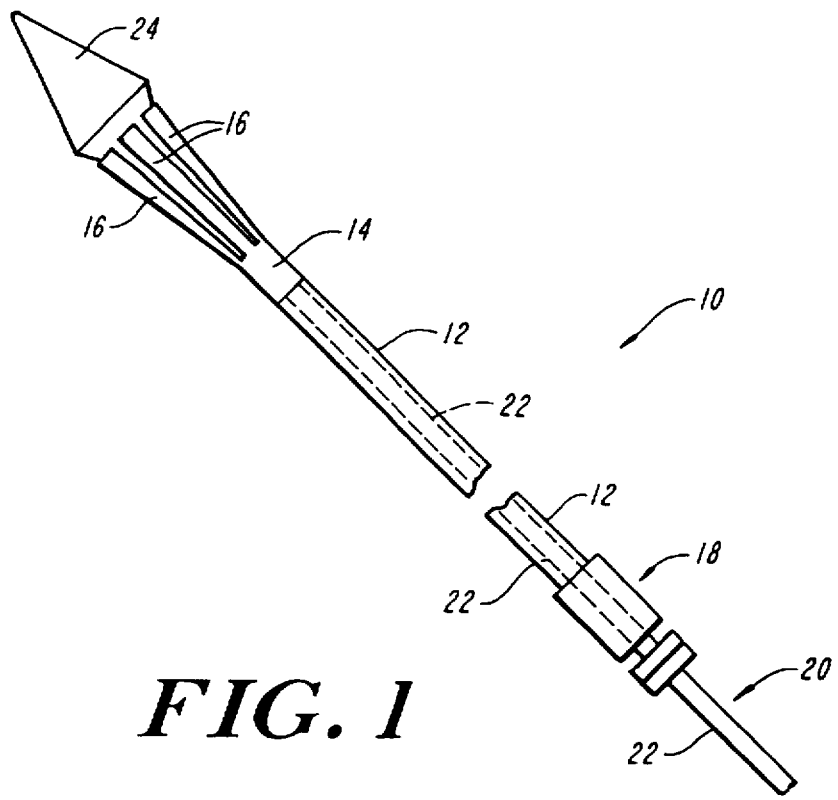
FIG. 1 illustrates a device of the present invention consisting of a catheter, an array or radially disposed wings disposed at a hollow fluted distal end of a catheter, and an expanding means for expanding the array of wings into a second enlarged configuration.

The devices and methods of the present invention enable the simple and accurate diagnostic testing of the constrictive force of the walls of the body lumens and, in particular, urethral sphincters and similar valves. In one aspect of the present invention, the device 10 can consist of a catheter 12 with a hollow fluted distal end 14 including an array of radially disposed wings 16, as shown in FIG. 1. The device 10 can also include a means 20 for expanding the array of wings 16 from a first configuration into a second enlarged configuration such that subsequent withdrawal of the catheter 12 from a body lumen encounters resistance which can be measured as an indication of the lumen's weakness. The expanding means 20 can include a retracting cable 22 disposed within and extending beyond the proximal end 18 of the catheter 12. This expanding means 20 can further include a plunger distal end 24 extending beyond the hollow fluted distal end 14 of the catheter 12. The plunger distal end 24 can be shaped to facilitate insertion into a body lumen.

Figure 2A:
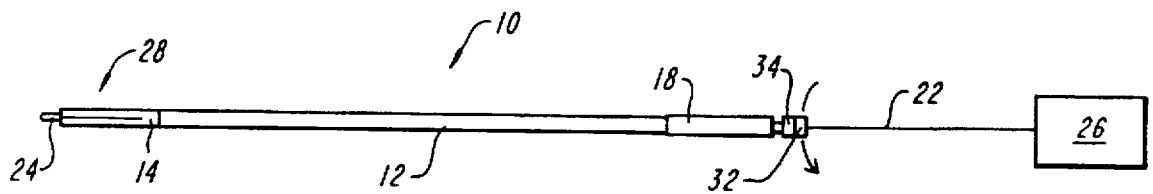
FIGS. 2A through 2B illustrate an activation means for activating a retracting cable disposed inside of a catheter such that a plunger distal end of the retracting cable is drawn into and expands an array of wings disposed at a hollow fluted distal end of a catheter from a first configuration into an enlarged second configuration.
Figure 2B:
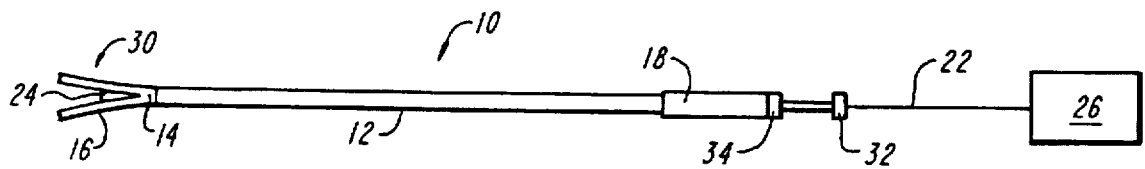

FIGS. 2A through 2B illustrate that the device 10 can further include a means 26 for activating the retracting cable 22 such that the plunger distal end 24 of the retracting cable 22 is drawn into and expands the array of wings 16 of the hollow fluted distal end 14 of the catheter 12 from a first configuration 28 into an enlarged second configuration 30. The device can include a screw 32 to open the proximal end 18 of the catheter to allow the activating means 26 to activate the retracting cable 22. The device can also include a set-screw or lock nut 34 disposed at the proximal end 18 of the catheter 12 for restricting the extent of the activation of the retracting cable 22 to a pre-determined extent.

Figure 3A:
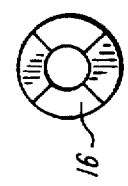
FIGS. 3A through 3D show enlarged frontal views of wings of a hollow fluted distal end of a catheter being expanded from a first configuration into three different enlarged second configurations.
Figure 3B:
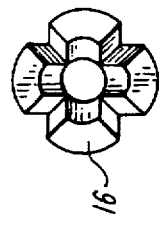
Figure 3C:
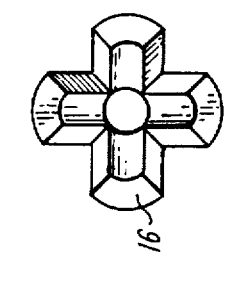
Figure 3D:
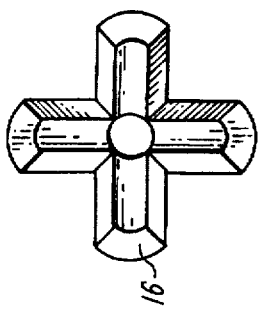
Figure 3E:
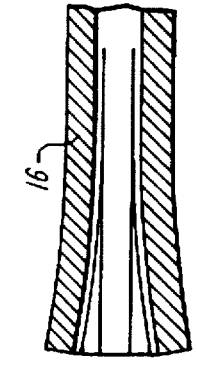
FIGS. 3E through 3H show corresponding enlarged side views of these wings being expanded from a first configuration into three different enlarged second configurations.
Figure 3F:
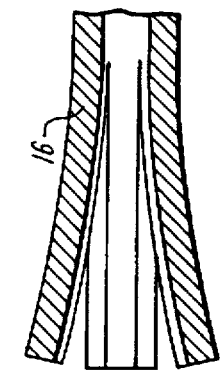
Figure 3G:
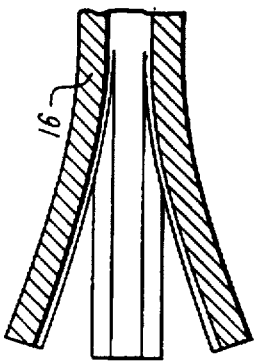
Figure 3H:
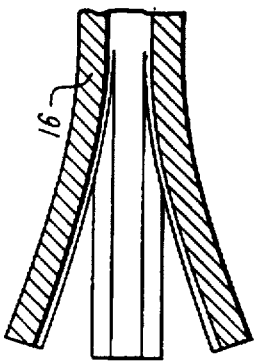

FIGS. 3A through 3D show enlarged frontal views of the wings 16 of the hollow fluted distal end 14 of the catheter 12 being expanded from a first configuration 28 into three different enlarged second configurations 30. FIGS. 3E through 3H show corresponding enlarged side views of the wings 16 of the hollow fluted end 14 of the catheter 12 being expanded from a first configuration 28 into three different enlarged second configurations 30. FIGS. 3D and 3H show a maximum expansion of the wings 16 of about 30 french.

Figure 4A:
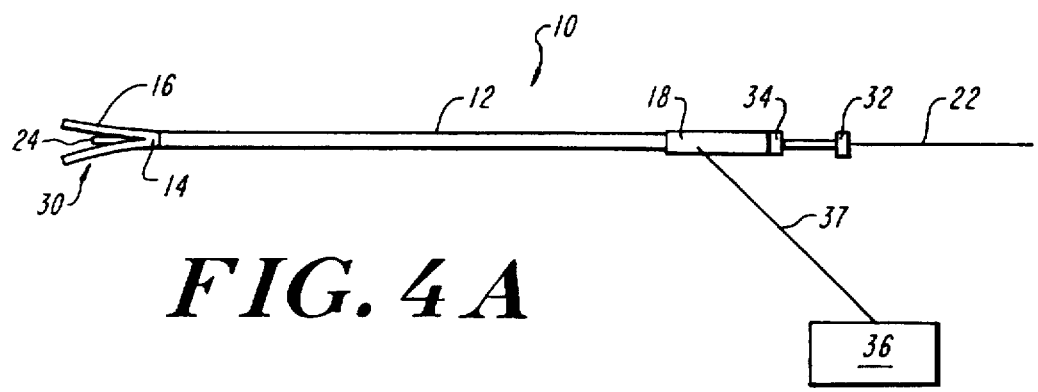
FIG. 4A illustrates a withdrawal means for withdrawing a catheter from a body lumen with a cable at a pre-determined rate.
Figure 4B:
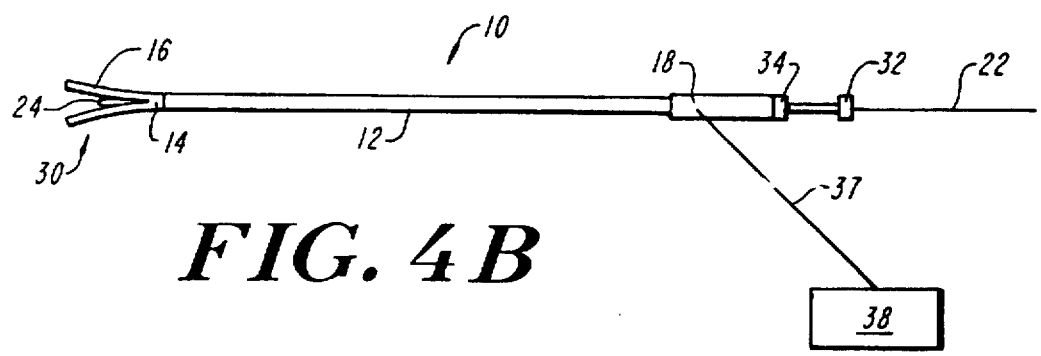
FIG. 4B illustrates a resistance monitor for measuring the resistance of withdrawal of a catheter from a body lumen as an indication of the lumen weakness.

The device 10 of the invention can include a withdrawal means 36 for withdrawing the catheter 12 from a body lumen with a cable 37 at a pre-determined rate, as shown by FIG. 4A. FIG. 4B illustrates that the device 10 of the present invention can also include a resistance monitor 38 for measuring the resistance to withdrawal of the catheter 12 from a body lumen as an indication of the weakness of the body lumen, e.g., by measuring the tension on cable 39.

Figure 5:
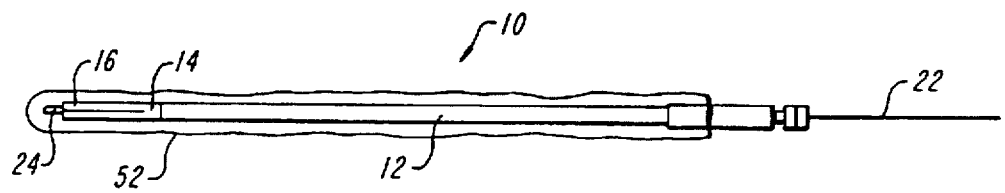
FIG. 5 shows a sterilizable device of the present invention including a disposable plastic sheath surrounding the outside of the device.

The device 10 of the present invention can be disposable. Alternatively, FIG. 5 shows that the device 10 of the present invention can be sterilizable and can further include a disposable plastic sheath 52 surrounding the outside of the device.

Figure 6:
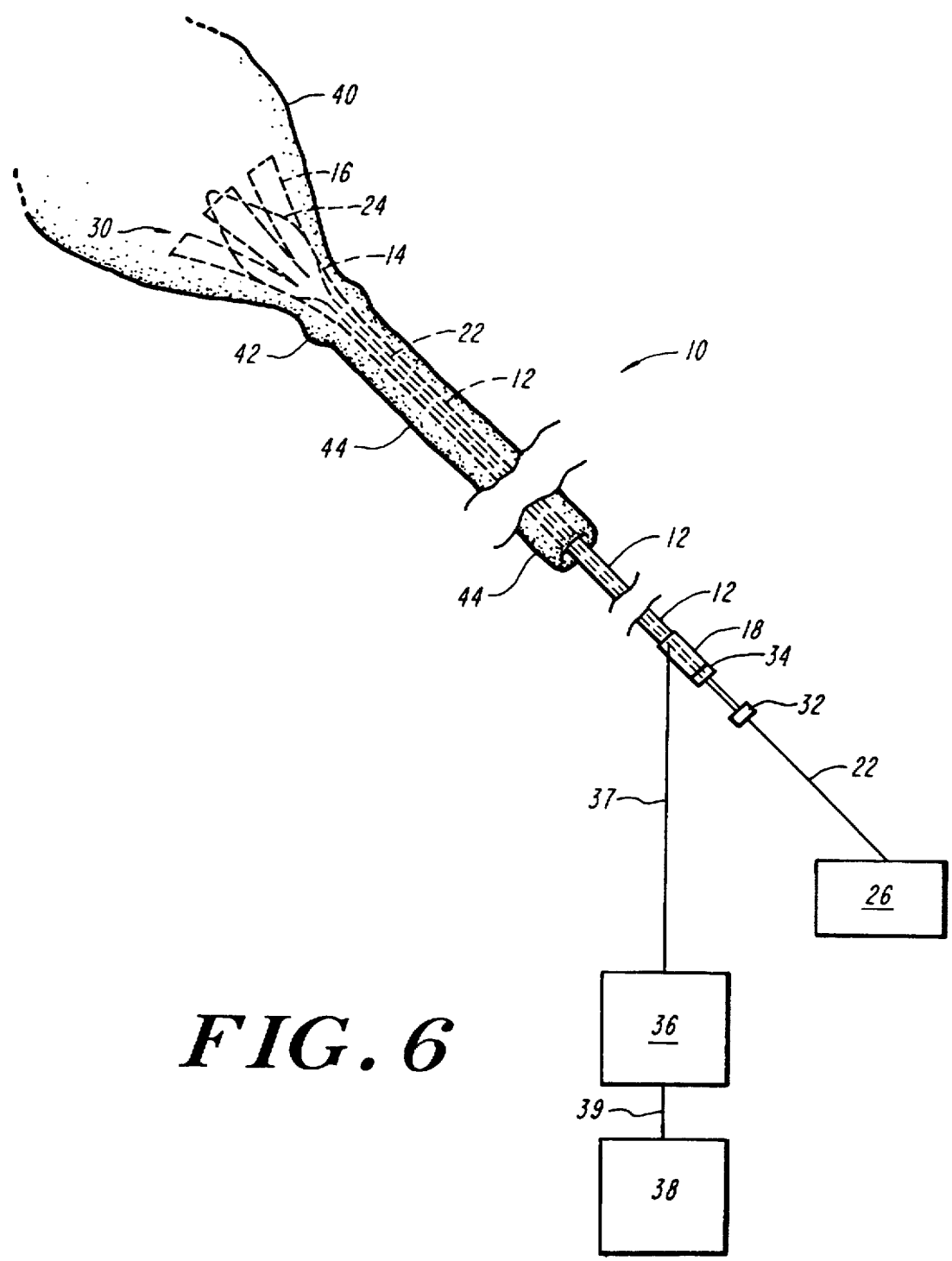
FIG. 6 illustrates a device for measuring the weakness of a urethral sphincter.

In another aspect of the present invention, the device 10 can measure the weakness of a sphincter 42 in a urethra 44, as shown by FIG. 6. FIG. 6 illustrates the plunger distal end 24 of the retracting cable 22 drawn into and expanding the wings 16 of the hollow fluted distal end 14 of catheter 12 into an enlarged second configuration 30. FIG. 6 also shows that the device 10 can be equipped with a screw 32 at the proximal end of the catheter 12 to open up the catheter for the activating means 26 to draw the plunger distal end 24 of the retracting cable 22 into the wings 16 of the hollow fluted distal end 14 of the catheter 12. FIG. 6 further shows that the device 10 can include a restriction means, such as a set-screw or lock nut 34 for restricting the extent of activation of the retracting cable 22. In addition, FIG. 6 shows that the device 10 can include a withdrawal device 36 for withdrawing the catheter 12 from the urethra 44 via cable 37 at a pre-determined rate and a resistance monitor 38 for measuring the resistance to withdrawal of the catheter 12 from the bladder 40 via cable 39 as an indication of the weakness of the urethral sphincter 42.

Figure 7:
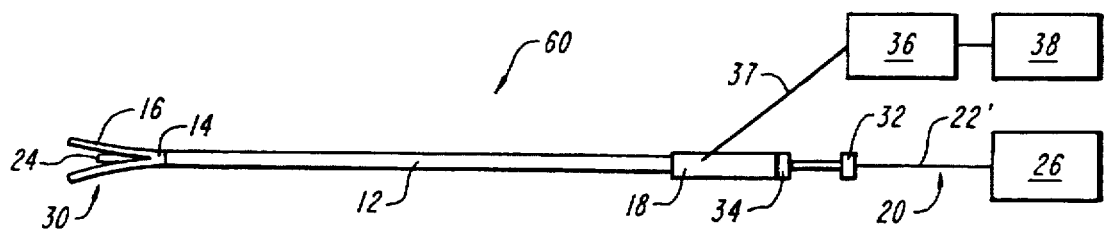
FIG. 7 illustrates a system for measuring the weakness of a body lumen consisting of a catheter with a hollow fluted distal end, a means for expanding the catheter's hollow fluted distal end from a first configuration into a second enlarged configuration, and a means for measuring resistance to withdrawal of the catheter in the enlarged second configuration as an indication of weakness of the body lumen.

In still another aspect of the present invention, a system 60 for measuring the weakness of a body lumen can include a catheter 12 with a hollow fluted distal end 14, a means 20 for expanding the catheter's hollow fluted distal end 14 from a first configuration into a second enlarged configuration, and a means 38 for measuring resistance to withdrawal of the catheter in the enlarged configuration as an indication of weakness of the body lumen, as shown by FIG. 7. FIG. 7 illustrates that the expanding means 20 of the system can include a retracting cable 22 disposed within the catheter 12 and extending beyond the proximal end 18 of the catheter 12, and a plunger distal end 24 of the retracting cable extending beyond the hollow fluted distal end 14 of the catheter. FIG. 7 shows the plunger distal end 24 of the retracting cable 22 drawn into and expanding radially disposed wings 16 on the hollow fluted distal end 14 of catheter 12 into an enlarged second configuration 30. FIG. 7 also shows that the system can be equipped with a screw 32 at the proximal end 18 of the catheter 12 to open up the catheter for the activating means 26 to draw the plunger distal end 24 of the retracting cable 22 into the wings 16 of the hollow fluted distal end 14 of the catheter 12. FIG. 7 further shows that the system 60 can include a set-screw or lock nut 34 for restricting the extent of activation of the retracting cable 22. In addition, FIG. 7 shows that the device 10 can include a withdrawal device 36 for withdrawing the catheter 12 from the body lumen via cable 37 at a pre-determined rate.

In sum, the present invention benefits from the recognition that measuring the resistance to withdrawal of an expandable distal end of a catheter from a body lumen provides a simple and accurate test for diagnosing lumen weakness. Further, the devices and methods of the present invention have advantages over the traditional techniques for measuring the weakness of body lumens, and urethral sphincters and similar valves in particular. Traditional techniques may involve the use of electrodes and/or the measurement of pressure exerted on a fluid in a catheter. In contrast, the devices and methods of the present invention involve measuring the resistance to withdrawal of a hollow fluted distal end of a catheter expanded into an enlarged configuration. Thus, the devices and methods of the present invention are simple and accurate and avoid the complications and awkwardness involved with using electrodes and/or fluid filled catheters to measure lumen weakness.

It will be understood that the above description pertains to only several embodiments of the present invention. That is, the description is provided by way of illustration and not by way of limitation. The invention is further characterized according to the following claims.

What is claimed is:

1. A method for measuring the constrictive force of a wall of a body lumen comprising:

inserting a catheter into the body lumen;

expanding a hollow fluted distal end of the catheter into an enlarged configuration where the fluted distal end contacts the wall of the body lumen; and measuring a resistance to withdrawal of the catheter in the enlarged configuration as an indicator of the constrictive force of a wall of the body lumen.

2. The method of claim 1 wherein the step of inserting the catheter into the body lumen further comprises simultaneously inserting a retracting cable inside the catheter into the body lumen such that a plunger distal end of the retracting cable extends beyond the hollow fluted distal end of the catheter.

3. The method of claim 2 wherein the step of expanding the hollow fluted distal end of the catheter further comprises activating the retracting cable such that the plunger distal end of the retracting cable is drawn into and expands a plurality of wings disposed at the hollow fluted distal end of the catheter.

4. The method of claim 3 wherein the step of activating the retracting cable further comprises activating the retracting cable to a pre-determined extent.

5. The method of claim 1 wherein the step of expanding the hollow fluted distal end of the catheter further comprises increasing the diameter of the hollow fluted distal end of the catheter to at least about 4 french.

6. The method of claim 1 wherein the step of measuring resistance further comprises measuring resistance with a resistance monitor.

7. The method of claim 1 wherein the step of measuring resistance further comprises withdrawing the catheter at a predetermined rate.

8. The method of claim 1, wherein the catheter in the inserting step is surrounded on the outside with a disposable plastic sheath prior to insertion of the catheter into the body lumen.

9. A method for measuring the constrictive force of a urethral sphincter comprising:

inserting a catheter into a bladder via the urethral sphincter;

expanding a hollow fluted distal end of the catheter into an enlarged configuration where the fluted distal end contacts the urethral sphincter; and measuring resistance to withdrawal of the catheter in the enlarged configuration as an indicator of constrictive force of the urethral sphincter.

10. The method of claim 9 wherein the step of inserting the catheter into the bladder further comprises simultaneously inserting a retracting cable inside the catheter into the bladder such that a plunger distal end of the retracting cable extends beyond the hollow fluted distal end of the catheter.

11. The method of claim 10 wherein the step of expanding the hollow fluted distal end of the catheter further comprises activating the retracting cable such that the plunger distal end of the retracting cable is drawn into and expands a plurality of wings disposed at the hollow fluted distal end of the catheter.

12. The method of claim 11 wherein the step of activating the retracting cable from the catheter further comprises activating the retracting cable to a pre-determined extent.

13. The method of claim 9 wherein the step of expanding the hollow fluted distal end of the catheter further comprises increasing the diameter of the hollow fluted distal end of the catheter to at least about 4 french.

14. The method of claim 9 wherein the step of measuring resistance further comprises measuring resistance with a resistance monitor.

15. The method of claim 9 wherein the step of measuring resistance further comprises withdrawing the catheter at a predetermined rate.

16. The method of claim 9, wherein the catheter in the inserting step is surrounded on the outside with a disposable plastic sheath prior to insertion of the catheter into the bladder.

17. A device for measuring the constrictive force of a wall of a body lumen comprising:

a catheter;

a hollow fluted distal end of the catheter with an array of wings radially disposed, the array of wings being closed in a first configuration and being radially expanded in a second enlarged configuration where the fluted distal end contacts the wall of the body lumen; and means for expanding the array of wings of the hollow fluted distal end into the second enlarged configuration such that subsequent withdrawal of the hollow fluted distal end in the second enlarged configuration encounters resistance which can be measured as an indication of the constrictive force of a wall of the body lumen.

18. The device of claim 17 wherein the means for expanding the array of wings of the hollow fluted distal end of the catheter further comprises:

a retracting cable disposed inside the catheter; and a plunger distal end of the retracting cable extending beyond the hollow fluted distal end of the catheter.

19. The device of claim 18, further comprising:

means for activating the retracting cable such that the plunger distal end of the retracting cable is drawn into and expands the wings of the hollow fluted distal end of the catheter into the second enlarged configuration.

20. The device of claim 19, further comprising:

restriction means disposed at a proximal end of the catheter for restricting the extent of the activation of the retracting cable to a pre-determined extent.

21. The device of claim 18 wherein the plunger distal end of the retracting cable further comprises a shape to facilitate insertion into the body lumen.

22. The device of claim 17, further comprising:
a resistance monitor for measuring the resistance of the withdrawal of the catheter.

23. The device of claim 17, further comprising:
a withdrawal means for withdrawing the catheter at a pre-determined rate.

24. The device of claim 17 wherein the device is disposable.

25. The device of claim 17, further comprising:
a disposable plastic sheath surrounding the outside of the device; and a sterilizable catheter.

26. A system for measuring the constrictive force of a wall of a body lumen comprising:
a catheter;
a means for expanding a hollow fluted distal end or the catheter from a first configuration into a second enlarged configuration where the fluted distal end contacts the wall of the body lumen; and
a means for measuring resistance to withdrawal of the catheter in the enlarged configuration as an indicator of constrictive force of a wall of the body lumen.

27. The system of claim 26 wherein the means for expanding the hollow fluted distal end of the catheter further comprises:
a retracting cable disposed inside the catheter; and
a plunger distal end of the retracting cable extending beyond the hollow fluted distal end of the catheter.

28. The system of claim 27, further comprising:
a means for activating the retracting cable such that the plunger distal end of the retracting cable is drawn into and expands a plurality of wings disposed at the hollow fluted distal end of the catheter into the second enlarged configuration.

29. The system of claim 28, further comprising:
restriction means disposed at a proximal end of the catheter for restricting the activation of the retracting cable to pre-determined extent.

30. The system of claim 27 wherein the plunger distal end of the retracting cable further comprises a shape to facilitate insertion into the body lumen.

31. The system of claim 26 wherein the hollow fluted distal end of the catheter further comprises an array of wings radially disposed, the array of wings being closed in the first configuration and being radially expanded in the second enlarged configuration.

32. The system of claim 26, further comprising:
a means for withdrawing the catheter at a predetermined rate.

33. The system of claim 26, further comprising:
a sterilizable catheter; and
a disposable plastic sheath surrounding the outside of the catheter.

34. A method for measuring constrictive force of a wall of a of a body lumen comprising:
inserting a catheter into the body lumen
inserting a retracting cable inside the catheter into the body lumen such that a plunger distal end of the retracting cable extends beyond a hollow fluted distal end of the catheter;
expanding the hollow fluted distal end of the catheter into an enlarged configuration where the fluted distal end contacts the wall of the body lumen; and
measuring a resistance to withdrawal of the catheter in the enlarged configuration as an indicator of constrictive force of the wall of the body lumen.

35. The method of claim 34 wherein the step of expanding the hollow fluted distal end of the catheter further comprises activating the retracting cable such that the plunger distal end of the retracting cable is drawn into and expands a plurality of wings disposed at the hollow fluted distal end of the catheter.

36. The method of claim 35 wherein the step of activating the retracting cable further comprises activating the retracting cable to a pre-determined extent.

37. A method for measuring constrictive force of wall of a body lumen comprising:
inserting a catheter into a body lumen, said catheter being surrounded on the outside with a disposable plastic sheath forming a surrounded catheter;
expanding a hollow fluted distal end of the surrounded catheter into an enlarged configuration where the fluted distal end contacts the wall of the body lumen; and
measuring a resistance to withdrawal of the surrounded catheter in the enlarged configuration as an indicator of constrictive force of a wall of the body lumen.

38. A method for measuring constrictive force of a urethral sphincter comprising:
inserting a catheter into a bladder via the urethral sphincter;
inserting a retracting cable inside the catheter into the bladder such that a plunger distal end of the retracting cable extends beyond a hollow fluted distal end of the catheter;
expanding a hollow fluted distal end of the catheter into an enlarged configuration where the fluted distal end contacts the urethral sphincter; and
measuring resistance to withdrawal of the catheter in the enlarged configuration as an indicator of constrictive force of the urethral sphincter.

39. The method of claim 38 wherein the step of expanding the hollow fluted distal end of the catheter further comprises activating the retracting cable such that the plunger distal end of the retracting cable is drawn into and expands a plurality of wings disposed at the hollow fluted distal end of the catheter.

40. The method of claim 39 wherein the step of activating the retracting cable from the catheter further comprises activating the retracting cable to a pre-determined extent.

41. A method for measuring weakness of a urethral sphincter comprising:
inserting a catheter into a bladder via the urethral sphincter, said catheter being surrounded on the outside with a disposable plastic sheath forming a surrounded catheter;
expanding a hollow fluted distal end of the surrounded catheter into an enlarged configuration; and
measuring resistance to withdrawal of the surrounded catheter in the enlarged configuration as an indicator of weakness of the urethral sphincter.

42. A device for measuring constrictive force of a wall of a body lumen comprising:
a catheter;
a hollow fluted distal end of the catheter with an array of wings radially disposed, the array of wings being closed in a first configuration and being radially expanded in a second enlarged configuration where the fluted distal end contacts the wall of the body lumen; and
means for expanding the array of wings of the hollow fluted distal end into the second enlarged configuration such that subsequent withdrawal of the hollow fluted distal end in the second enlarged configuration encounters resistance which can be measured as an indication of weakness of the body lumen, wherein the means for expanding comprises a retracting cable disposed inside the catheter and a plunger distal end of the retracting cable extending beyond the hollow fluted distal end of the catheter.

43. The device of claim 42, further comprising:

means for activating the retracting cable such that the plunger distal end of the retracting cable is drawn into and expands the wings of the hollow fluted distal end of the catheter into the second enlarged configuration.

44. The device of claim 43, further comprising:

restriction means disposed at a proximal end of the catheter for restricting the extent of the activation of the retracting cable to a predetermined extent.

45. The device of claim 42 wherein the plunger distal end of the retracting cable further comprises a shape to facilitate insertion into the body lumen.

46. A device for measuring constrictive force of a wall of a body lumen comprising:

a sterilizable catheter;

a hollow fluted distal end of the catheter with an array of wings radially disposed, the array of wings being closed in a first configuration and being radially expanded in a second enlarged configuration where the fluted distal end contacts the wall of the body lumen;

means for expanding the array of wings of the hollow fluted distal end into the second enlarged configuration such that subsequent withdrawal of the hollow fluted distal end in the second enlarged configuration encounters resistance for indicating constrictive force of the wall of the body lumen; and a disposable plastic sheath surrounding the outside of the device.

47. A system for measuring constrictive force of a wall of a body lumen comprising:

a catheter;

a means for expanding a hollow fluted distal end of the catheter from a first configuration into a second enlarged configuration where the fluted distal end contacts the wall of the body lumen; wherein the means for expanding comprises a retracting cable disposed inside the catheter and a plunger distal end of the retracting cable extending beyond the hollow fluted distal end of the catheter; and a means for measuring resistance to withdrawal of the catheter in the enlarged configuration as an indicator of constrictive force of a wall of the body lumen.

48. The system of claim 47, further comprising:

a means for activating the retracting cable such that the plunger distal end of the retracting cable is drawn into and expands a plurality of wings disposed at the hollow fluted distal end of the catheter into the second enlarged configuration.

49. The system of claim 48, further comprising:

restriction means disposed at a proximal end of the catheter for restricting the activation of the retracting cable to pre-determined extent.

50. The system of claim 47 wherein the plunger distal end of the retracting cable further comprises a shape to facilitate insertion into the body lumen.

51. A system for measuring constrictive force of a wall of a body lumen comprising:

a sterilizable catheter;

a disposable plastic sheath surrounding the outside of the catheter.

a means for expanding a hollow fluted distal end of the catheter from a first configuration where the fluted distal end contacts the wall of the body lumen into a second enlarged configuration; and a means for measuring resistance to withdrawal of the catheter in the enlarged configuration as an indicator of constrictive force of a wall of the body lumen.

* * * * *